United States Patent [19]

Saccomano et al.

[11] Patent Number: 4,861,891
[45] Date of Patent: Aug. 29, 1989

[54] ANTIDEPRESSANT N-SUBSTITUTED NICOTINAMIDE COMPOUNDS

[75] Inventors: Nicholas A. Saccomano, Ledyard; Frederic J. Vinick, Waterford, both of Conn.

[73] Assignee: Pfizer Inc., New York, N.Y.

[21] Appl. No.: 238,951

[22] Filed: Aug. 31, 1988

[51] Int. Cl.$^4$ ............................................. C07D 401/12
[52] U.S. Cl. .................................... 546/194; 546/273; 546/291
[58] Field of Search .................... 546/291, 194, 273

[56] References Cited

U.S. PATENT DOCUMENTS

| | | | |
|---|---|---|---|
| 4,251,263 | 2/1981 | Gutman | 71/94 |
| 4,270,946 | 6/1981 | Gutman | 71/94 |
| 4,618,366 | 10/1986 | Cramp et al. | 71/94 |

Primary Examiner—Richard A. Schwartz
Attorney, Agent, or Firm—Peter C. Richardson; J. Trevor Lumb; Albert E. Frost

[57] ABSTRACT

Certain N-substituted nicotinamide compounds having formula (I) below

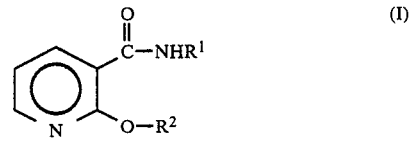

and pharmaceutically acceptable acid addition salts thereof wherein $R^1$ is 1-piperidyl, 1-(3-indolyl)ethyl, $C_{1-4}$ alkyl, phenyl, 1-(1-phenylethyl), benzyl or monosubstituted benzyl wherein the substituent is methyl, methoxy, chloro or fluoro; and $R^2$ is bicyclo[2.2.1]hept-2-yl or

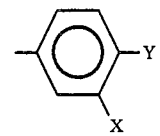

wherein Y is hydrogen, fluoro or chloro; and X is hydrogen, fluoro, chloro, methoxy, trifluoromethyl, cyano, carboxy, carbo ($C_{1-4}$ alkoxy), methylcarbamoyl or dimethylcarbamoyl function as selective inhibitors of calcium-independent phosphodiesterase and are useful as antidepressants.

5 Claims, No Drawings 4,861,891

ANTIDEPRESSANT N-SUBSTITUTED NICOTINAMIDE COMPOUNDS

BACKGROUND OF THE INVENTION

1. Field of the Invention

This invention relates to antidepressant compounds having the formula

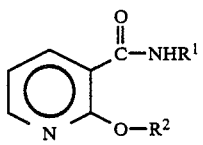

and pharmaceutically acceptable acid addition salts thereof wherein $R^1$ is 1-piperidyl, 1-(3-indolyl)ethyl, alkyl, phenyl, benzyl, substituted benzyl or 1-(1-phenylethyl); and $R^2$ is bicyclo[2.2.1]hept-2-yl, phenyl, meta- and/or para-substituted phenyl, to compositions containing them, and to their use as antidepressants.

2. Description of the Prior Art

U.S. Pat. No. 4,251,263 describes a series of herbicidal N-substituted 2-phenoxynicotinamides of the formula

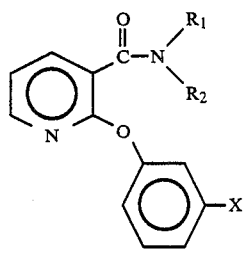

wherein X is chloro, bromo, trifluoromethyl, methyl or ethyl; $R_1$ is hydrogen or $C_3-C_5$ alkenyl; and $R_2$ is (a) $C_3-C_5$ alkenyl if $R_1$ is $C_3-C_5$ alkenyl; (b) $C_3-C_5$ alkyl, $C_3-C_5$ alkenyl or $C_3-C_6$ alkynyl if X is chloro, methyl, ethyl or trifluoromethyl and $R_1$ is hydrogen; and (c) $C_1-C_5$ alkyl, $C_3-C_5$ alkenyl or $C_3-C_6$ alkynyl if X is bromo and $R_1$ is hydrogen.

Herbicidal N-arylphenoxynicotinamide derivatives of the formula

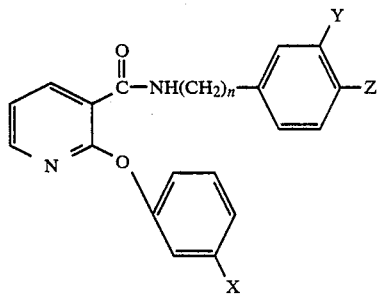

in which n is 0 or 1; X is halogen, $C_1-C_3$ alkyl, trifluoromethyl or carboethoxy; Y and Z are independently hydrogen, lower alkyl, halo-lower alkyl, thio(halo lower alkyl), lower alkoxy, nitro, cyano or halogen; provided that:

if X is carboethoxy, Z is halogen and Y is hydrogen or halogen; and if Y and Z are both halogen, X is halogen, trifluoromethyl or carboethoxy, are described in U.S. Pat. No. 4,270,946.

U.S. Pat. No. 4,618,366 discloses herbicidal nicotinamide derivatives of the formula

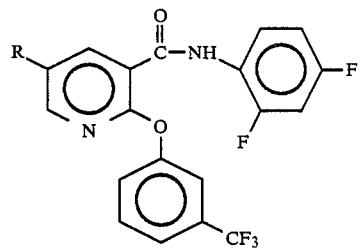

wherein R is hydrogen or methyl.

SUMMARY OF THE INVENTION

It has now been found that certain N-substituted nicotinamide compounds having formula (I) below

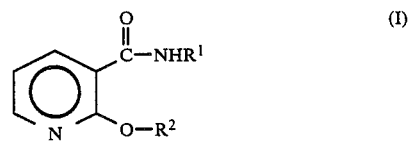

(I)

and pharmaceutically acceptable acid addition salts thereof wherein $R^1$ is 1-piperidyl, 1-(3-indolyl)ethyl, $C_{1-4}$ alkyl, phenyl, 1(1-phenylethyl), benzyl or mono-substituted benzyl wherein the substituent is methyl, methoxy, chloro and fluoro; and $R^2$ is bicyclo[2.2.1]hept-2-yl or

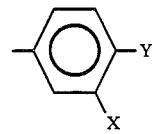

wherein Y is hydrogen, fluoro or chloro; and

X is hydrogen, fluoro, chloro, methoxy, trifluoromethyl, cyano, carboxy, carbo($C_{1-4}$ alkoxy), methylcarbamoyl or dimethylcarbamoyl are useful as antidepressants. They are selective inhibitors of calcium-independent phosphodiesterase and are useful as antidepressants.

Favored compounds are those wherein $R^1$ is benzyl or mono-substituted benzyl, and $R^2$ is 3-carbo($C_{1-4}$ alkoxy)phenyl. Preferred is the compound wherein $R^1$ is benzyl and $R^2$ is 3-carbomethoxyphenyl.

Also included in this invention are the novel compounds of formula (I) and their pharmaceutically acceptable acid addition salts. Further, pharmaceutical compositions comprising formula (I) compounds and/or their acid addition salts and their use as antidepressants are embraced within the present invention. Still further, methods for making formula (I) compounds are included within this invention.

Said novel compounds comprise those formula (I) compounds wherein $R^1$ is 1-piperidyl, 1-(3-indolyl)ethyl, $(C_{1-4})$-alkyl, phenyl, benzyl, 1-(1-phenylethyl) or monosubstituted benzyl wherein the substituent is chloro, fluoro, methyl or methoxy;

$R^2$ is bicyclo[2.2.1]hept-2-yl or

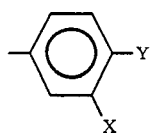

wherein Y is hydrogen, fluoro or chloro; and

X is hydrogen, fluoro, chloro, methoxy, trifluoromethyl, cyano, carboxy, methylcarbamoyl, dimethylcarbamoyl or carbo($C_{1-4}$ alkoxy);

provided that when $R^1$ is phenyl, benzyl, monosubstituted benzyl, 1-(1-phenylethyl) or ($C_{1-4}$)alkyl, $R^2$ is bicyclo[2.2.1]hept-2-yl.

When depicted by formula hereinafter, novel compounds of formula (I) represent novel values of variables $R^1$ and $R^2$ as variables $R^3$ and $R^4$, respectively, i.e. compounds of the following formula

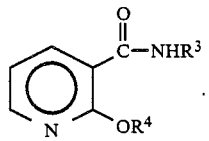

Suitable compounds with the above formula include those wherein $R^3$ is 1-piperidyl or 1-(3-indolyl)ethyl, the compound wherein $R^3$ is 1-(3-indolyl)ethyl and $R^4$ is bicyclo[2.2.1]hept-2-yl, those compounds wherein $R^3$ is 1-piperidyl or 1-(3-indolyl)ethyl and $R^4$

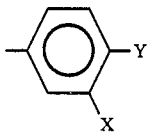

wherein Y is hydrogen and X is carbo($C_{1-4}$ alkoxy), and the compound wherein $R^3$ is 1-piperidyl and $R^4$ is

DETAILED DESCRIPTION OF THE INVENTION

As those skilled in the art will recognize, compounds of formula (I) can be made by various routes. They can, for example, be prepared by amidation of 2-chloronicotinic acid or a reactive derivative thereof, such as the acid chloride, a mixed ester, or by dehydrative coupling, with the appropriate amine $R^1NH_2$, followed by reaction of the N-substituted 2-chloronicotinamide product with the appropriate phenol (or alcohol) $R^2OH$ via the Williamson reaction.

Alternatively, the 2-chloronicotinic acid can first be converted to the desired ether derivative via the Williamson reaction and the thus-produced ether converted to an amide of formula (I) according to procedures described above.

The amidation reaction described above is conveniently carried out by reacting equimolar amounts of 2-chloronicotinic acid, or the appropriate 2-$R^2O$ nicotinic acid derivative, in a reaction-inert solvent such as tetrahydrofuran with isobutyl chloroformate (or other $C_{1-4}$ alkyl chloroformate) in the presence of N-methylmorpholine at −10° to 0° C. The desired amine (in a molar ratio of from 1:1 to 1:2 based upon the nicotinic acid reactant) is then added to the reaction at −10° to 0° C. and the reaction then gradually warmed to ambient temperature. The reaction is stirred until substantially complete and the product recovered by known procedures.

Formation of the ether derivatives from 2-chloronicotinic acid or from the appropriate N-substituted 2-chloronicotinamide is readily achieved via the Williamson reaction. The phenol, or alcohol, reactant $R^2OH$ is converted to an alkoxide by reaction with a base such as sodium hydride in a reaction-inert solvent at ambient temperature. An exothermic reaction occurs with evolution of gas. The appropriate 2-chloronicotinic acid reactant is added and, when gas evolution is complete, the reaction is heated to reflux until substantially complete. The product is recovered by known procedures. Dimethylformamide serves as satisfactory solvent for this reaction.

The acid addition salts of formula (I) compounds are readily prepared by adding at least a stoichiometric amount of the appropriate acid to a formula (I) compound in a solvent, preferably one in which the formula (I) compound is at least partially soluble. The acid addition salt, if soluble in the solvent system, is recovered by evaporation of the solvent or by addition of a non-solvent for the salt to precipitate it from the reaction solvent.

The compounds of formula (I) above and their salts exhibit increased duration of action versus rolipram, 4-[3-(cyclopentyloxy)-4-methoxyphenyl]-2-pyrrolidinone, which is described in U.S. Pat. No. 4,193,926. Their biochemical and behavioral profiles are similar to those of rolipram.

The compounds of this invention having formula (I) function as calcium independent c-AMP phosphodiesterase inhibitors and are useful as antidepressants. Their activity as calcium independent c-AMP phosphodiesterase inhibitors is determined by the method of Davis, Biochimica et Biophysica Acta. 797, 354-362 (1984). In this procedure, calcium-independent and dependent phosphodiesterases (IPDE and DPDE, respectively) are ZO prepared from cerebral cortices of female Sprague-Dawley rats by first homogenizing the brain tissue in a pH 7.5 20 mM Tris-HCl buffer also containing 1 mM $MgCl_2$, 3 mM 2-mercaptoethanol, and 0.1 mM EGTA (ethyleneglycol-bis-(beta-aminoethyl ether)-N,N'-tetraacetic acid). The homogenate is centrifuged at 105,000×g for 60 minutes, and the supernatant fluid containing the enzymes is passed through a column of Sephadex G-200 to separate IPDE from DPDE. The two phosphodiesterases are each further purified by affinity chromatography on a column of calmodulin-Sepharose.

Phosphodiesterase activity is determined using 0.1 ml reaction mixture containing Tris-HCl pH 7.5 buffer (5 μmol), $MgCl_2$ (0.5 μmol), and [3H]cAMP (New England Nuclear, NET-275). The final concentration of cAMP is 1.0 μM (containing 400,000 dpm of

[3H]cAMP). Ten μl of vehicle or inhibitor solution and 10 μl of fresh IPDE or DPDE or the respective boiled enzymes are added to 80 μl of substrate in the Tris-HCl/MgCl$_2$ buffer. The reaction mixtures are incubated for 8 minutes at 37° C. and placed in a hot water bath for 2 minutes to stop hydrolysis of cAMP. Carrier 5'-AMP (0.5 ml of 0.5 mM 5'-AMP in 0.1 M Hepes (N-2-hydroxyethylpiperazine-N'-2-ethanesulfonic acid)-0.1 M NaCl pH 8.5 buffer) are added, and the contents of the incubation tubes placed on columns of polyacrylamide-boronate affinity gel (BIO-RAD Affi-Gel 601 Boronate Gel). The unreacted [3H]cAMP is eluted from the gel with 7.5 ml of the 0.1M Hepes-NaCl buffer. The [3H]cAMP is eluted from the gel with 7.5 ml of the 0.1M Hepes-NaCl buffer. The [3H]5'-AMP product is eluted with 7 ml of 50 mM Na acetate buffer pH 4.8. One-ml aliquots of the latter eluates are counted in a liquid scintillation counter to determine their content of radioactive 5'-AMP.

When used for the treatment of depression and other various neurological and psychic disorders characterized by withdrawal, anxiety, thought-disturbances and delusion, they are used as is or in the form of pharmaceutical compositions comprising a formula (I) compound and pharmaceutically-acceptable carriers or diluents. For oral administration, the preferred route for administering said compounds, suitable pharmaceutical carriers include inert diluents or fillers, thereby forming dosage forms such as tablets, powders, capsules, and the like. These pharmaceutical compositions can, if desired, contain additional ingredients such as flavorings, binders, excipients and the like. For example, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials include lactose or milk sugar and high molecular weight polyethylene glycols.

For oral administration, the daily dose of active agent of formula (I) is from about 0.1 mg to about 10 mg., and for parenteral administration, preferably i.v. or i.m., from about 0.01 mg. to about 5 mg. The prescribing physician, of course, will ultimately determine the appropriate dose for a given human subject dependent upon factors such as the severity of the patient's symptoms and the patient's response to the particular drug.

The antidepressant activity of the compounds of this invention is determined by the behavioral despair paradigm described by Porsolt et al., Arch. Int. Pharmacodyn. 227, 327-336 (1977).

In this procedure a depressed state is induced in mice by forcing them to swim in a narrow water-containing cylinder from which there is no escape. The procedure involves injecting a mouse per os with the test compound and then (30 minutes post-injection) placing it in a standard 1 liter glass beaker containing 800 ml of 25 degree Centigrade water.

An observer then rates the animal's mobility (0=mobile; 1=immobile) every 30 seconds for 5 minutes beginning 2 minutes after being placed in the water. Male CD (Charles River) mice (10 per treatment) weighing 20-25 g are used as subjects. The compounds are administered in a solution (vehicle) containing 0.9% saline (90%), dimethyl sulfoxide (5%), and emul 4 (5%). All drugs are injected in a volume of 10 ml/kg. A vehicle treated mouse typically has a swim score of 9, while an antidepressant drug reduces the magnitude of immobility, resulting in a decrease in the swim score.

The second procedure is the method of Koe et al., J. Pharmacol. Exp. Therap. 226, 686-700 (1983) which comprises determination of the ability of a test drug to counteract reserpine hypothermia in mice. In this procedure, mice are placed in a room with an ambient temperature of 20° C. The mice are individually housed in plastic chambers with a cardboard bottom, injected with reserpine (1.0 mg/kg s.c.), and retained at 18°-19° C. for 18 hours. Their rectal temperatures are then ascertained, immediately after which they receive saline or drug treatment. Rectal temperatures are again measured, usually at 1, 2 and 4 hours after this second injection. Results are presented as the mean increase in reserpine-depressed temperature, expressed either as a percentage or an absolute increase. Typically, reserpine-pretreated mice given vehicle exhibit rectal temperatures averaging about 20°-22° C. 4 hours after administration of vehicle. Treatment with desipramine (10 mg/kg p.o.), a known antidepressant, yields temperatures averaging about 30°-33° C. (about a 40°-50% increase). Administration of formula (I) compounds brings about an increase in rectal temperature of the test mice.

The examples and below are provided solely for further illustration. The following abbreviations for peak shapes are used in reporting $^1$H-nmr values: bs, broad singlet; vbs, very broad singlet; s, singlet; d, doublet; t, triplet;, q, quartet, m, multiplet. In the Examples no effort was made to optimize the yield of any given reaction.

EXAMPLE 1

N-Benzyl-2-chloronicotinamide

2-Chloronicotinic acid (25 grams, 158.67 mmol) is placed into a 2L 4-neck round bottom flask equipped with mechanical stirring, thermometer, nitrogen inlet and a rubber septum and is charged with 800 ml of tetrahydrofuran (THF). The reaction is chilled to 0° C. N-methylmorpholine (16.05 grams, 158.67 mmol) is added via syringe. The reaction is chilled to −10° C. and isobutyl chloroformate (21.67 grams, 158.67 mmol) is added to the reaction via syringe while maintaining the temperature at less than 0° C. The reaction is allowed to stir at −10° C. for 30 minutes. Benzylamine (18.70 grams, 174.54 mmol) is then added via syringe while maintaining the temperature below 0° C. The reaction is allowed to slowly warm to room temperature. After stirring for 18 hours 1N HCl (300 ml) is added to the reaction. This is then extracted with ethyl acetate (2×350 ml). The organics are combined and washed with 1N HCl (1×300 ml) and 12% sodium hydroxide (2×300 ml). The organic layer is dried over anhydrous magnesium sulfate, filtered and concentrated to a white paste. The paste is triturated with diethyl ether to yield a solid. This is filtered and washed with diethyl ether (2×65 ml). The filtrates are concentrated and triturated with fresh diethyl ether to yield a second crop of compound which is combined with the first to yield 28.11 grams (71.8%) of N-benzyl-2-chloronicotinamide as a white crystalline solid.

m.p.: 120° C.

$^1$H NMR (300 MHz, CDCl): δ8.43 (dd, 1H, J=3 Hz, J=2 Hz), 8.11 (dd, 1H, J=6 Hz, J=2 Hz), 7.45-7.22 (m, 6H), 6.77 (bs, 1H), 4.65 (d, 2H).

EXAMPLE 2

N-Benzyl-2-(3-(Fluorophenoxy)nicotinamide

A. 2-(3-Fluorophenoxy)nicotinic Acid

Sodium hydride dispersion, 50% by weight (3.05 grams, 63.47 mmol) is placed into a 125 ml round bottom equipped with a stir bar and condenser under nitrogen and is charged with 32 ml of dimethylformamide. 3-Fluorophenol (3.56 grams, 31.73 mmol) is added portionwise over five minutes. During this addition, an exotherm and vigorous gas evolution is observed. The reaction is allowed to stir for five minutes. 2-Chloronicotinic acid (5.00 grams, 31.73 mmol) is added portionwise over five minutes. Gas evolution is observed. When it subsides, the reaction is heated to reflux for 2 hours. The reaction is cooled to room temperature and 300 ml of water is added. The aqueous layer is extracted with diethyl ether (2×200 ml). The aqueous layer is then pH adjusted to acidic with glacial acetic acid and extracted with ethyl acetate (3×150 ml). The organics are combined and washed with water (2×150 ml). The organic layer is dried over anhydrous magnesium sulfate, filtered and concentrated in vacuo to yield a yellow oil. The oil is purified by trituration with diethyl ether/hexanes (3/1) to yield 1.42 grams (19.2%) of product as a yellow crystalline solid.

High resolution mass spec (233.0476/157) indicates that unreacted starting material and product co-crystallized. The crude material is carried on to step B.

B. N-Benzyl-2-(3-Fluorophenoxy)nicotinamide

The aryloxynicotinic acid (1.32 grams, 5.66 mmol) from Part A is placed into a 200 ml 3-neck round bottom flask equipped with magnetic stir bar, thermometer, nitrogen inlet and a rubber septum and is charged with 30 ml of THF. N-methylmorpholine (0.57 grams, 5.66 mmol) is added via syringe. The reaction is chilled to −10° C. and isobutyl chloroformate (0.77 grams, 5.66 mmol) is added to the reaction via syringe while maintaining the temperature at less than 0° C. The reaction is allowed to stir at −10° C. for 30 minutes. Benzylamine (0.67 grams, 6.23 mmol) is then added via syringe while maintaining the temperature below 0° C. The reaction is allowed to slowly warm to room temperature. After stirring for 18 hours, water (100 ml) is added to the reaction. This is then extracted with ethyl acetate (2×100 ml). The organics are combined and washed with 2N sodium hydroxide (3×100 ml). The organic layer is dried over anhydrous magnesium sulfate, filtered and concentrated in vacuo to yield a yellow oil. The crude product is purified by flash chromatography using diethyl ether/hexanes (2/1) as the eluant to yield 0.66 grams (36.3%) of the desired aryloxynicotinamide as a white solid.

m.p.: 86°-86.5° C.

$^1$H NMR (250 MHz, CDCl$_3$): δ8.66 (dt, 1H, J=8 Hz, J=2 Hz), 8.24 (dt, 1H, J=3 Hz, J=1 Hz), 8.22 (bs, 1H), 7.55-6.87 (m, 10H), 4.73 d, 2H).

Analysis Calcd. for C$_{19}$H$_{15}$N$_2$O$_2$F:C, 70.80, H, 4.69, N, 8.69. Found: C, 70.71, H, 4.61, N, 8.65.

EXAMPLE 3

N-[2-(3-Indolyl)ethyl]-2-(4-Fluorophenoxy)nicotinamide 2-(4-Fluorophenoxy)nicotinic acid (500 mg, 2.14 mmol) and 15 ml THF is placed in a 50 ml three neck round bottom flask with a magnetic stir bar, a thermometer and a rubber septum with a nitrogen inlet. The mixture is cooled to −5° C. and N-methyl morpholine (211 mg, 2.14 mmol) added via syringe. Isobutyl chloroformate (157 mg, 2.14 mmol) is then added via syringe while keeping the temperature below 0° C. The reaction mixture is allowed to stir at −5° C. for one hour, and tryptamine (377 mg, 2.35 mmol) is then added, again keeping the temperature below 0° C. The reaction is allowed to warm to room temperature and stirred for 18 hours, when 1M HCl (10 ml) is added. This is then extracted with ethyl acetate (2×20 ml) and the combined organics washed with 1M HCl (1×20 ml), 3M NaOH (2×20 ml), H$_2$O (1×30 ml) and brine (1×30 ml). The organic layer is dried over anhydrous sodium sulfate, filtered and concentrated to a yellow solid. This is then recrystallized in ethanol/ethyl acetate and dried in vacuo to yield 421 mg (52.4%) of the title aryloxynicotinamide as a white crystalline solid.

m.p. 194°-196° C.

$^1$H NMR (300 MHz, DMSO-d$_6$): δ8.45 (t, 1H), 8.14 (m, 2H), 7.56 (d, 1H, J=4 Hz), 7.36-6.90 (m, 8H), 3.64-3.54 (m, 2H), 3.35 (s, 1H), 2.96 (t, 2H).

Analysis Calcd. for C$_{22}$H$_{18}$O$_2$N$_3$F:C, 70.39; H, 4.83; N, 11.19. Found: C, 70.16; H, 4.84; N, 11.04.

HRMS 375.1390; Calcd for C$_{22}$H$_{18}$N$_3$O$_2$F 375.138.

EXAMPLE 4

N-(4-Fluorobenzyl)-2-Chloronicotinamide

2-Chloronicotinic acid (2.5 grams, 15.9 mmol) and 80 ml THF is placed in a 250 ml three neck round bottom flask equipped with mechanical stirring, a thermometer and a rubber septum with a nitrogen inlet. The reaction mixture is cooled to −5° C. and N-methylmorpholine (1.6 grams, 15.9 mmol) added via syringe. Isobutyl chloroformate (2.2 grams, 15.9 mmol) is then added via syringe while maintaining the temperature below 0° C. The reaction is stirred for 30 minutes at −5° C. The p-fluorobenzylamine (2.2 grams, 17.5 mmols) is then added via syringe, keeping the temperature below 0° C. The reaction is allowed to warm to room temperature and stirred for 18 hours, after which 1M HCl (30 ml) is added. This is then extracted with ethyl acetate (2×30 ml), and the combined organics washed with 1M HCl (1×30 ml), 3M NaOH (2×30 ml), H$_2$O (1×50 ml) and brine (1×50 ml). The organic layer is dried over anhydrous magnesium sulfate, filtered and concentrated to a yellow solid. This is triturated with diethyl ether, filtered, washed with fresh diethyl ether and dried in vacuo to yield 3.4 g (80.5%) of the desired chloronicotinamide as a white crystalline solid.

m.p.: 155°-157° C.

$^1$H NMR (300 MHz, CDCl$_3$): δ8.36 (m, 1H), 8.00 (dd, 1H, J=4 Hz, J=1Hz), 7.38-7.21 (m, 3H), 6.88 (t, 2H), 6.81 (bs, 1H), 4.47 (d, 2H, J=3 Hz).

In like manner, the following 2-chloronicotinamides of formula A are prepared from 2-chloronicotinic acid (2-CNA) and the appropriate amine (R$^1$NH$_2$):

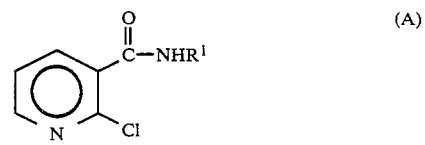

(A)

| 2-CNA | | | Yield of (A) | | | $^1$H NMR (300 MHz, CDCl$_3$) |
|---|---|---|---|---|---|---|
| G | mmol | R$^1$ | G | % | MP (°C.) | δ |
| 2.5 | 15.9 | C$_6$H$_5$ | 1.7 | 46.0 | 108–110 | 8.36 (m, 1 H), 7.96 (dd, 1 H, J = 4 Hz, J = 1 Hz), 7.26 (m, 1 H), 6.52–6.20 (bs, 1 H), 4.40–4.16 (m, 1 H), 3.22 (d, 6 H, J = 4 Hz) |
| 2.5 | 15.9 | 4-CH$_3$benzyl | 3.3 | 79.7 | 151–152.5 | 8.39 (m, 1 H), 8.05 (dd, 1 H, J = 4 Hz, J = 1 Hz), 7.40–7.04 (m, 5 H), 6.76 (bs, 1 H), 4.58 (d, 2 H, J = 3 Hz), 2.33 (s, 3 H) |
| 1.5 | 9.5 | 4-CH$_3$O benzyl | 1.8 | 68.5 | 109–111 | 8.35 (m, 1 H), 8.00(dd, 1 H, J = 4 Hz, J = 1 Hz), 7 H), (m, (m, 1 H), 6.82 (d, 3 H, J = 6 Hz), 6.77 (bs, 1 H), 4.52(d, 2 H, J = 4 Hz), 3.75 (s, 3 H) |
| 1.5 | 9.5 | 4-Cl benzyl | 2.0 | 74.9 | 177–179.5 | 8.41 (m, 1 H), 8.08 (dd, 1 H, J = 5 Hz, J = 1 Hz), 7.29 (m, 5H), 6.80 (bs, 1 H), 4.59 (d, 2 H, J = 5 Hz) |
| 2.0 | 12.7 | 1-piperidyl | 1.5 | 52.7 | yellow oil | 8.28 (m, 1 H), 7.50 (dd, 1 H, J = 4 Hz, J = 1 Hz), 7.18 (m, 1 H), 3.42–2.96 (m, 4 H), 1.70–1.30 (m, 6H) |
| 2.0 | 12.7 | 1-(1-phenethyl) | 2.5 | 75.4 | 136–138 | 8,17 (m, 1 H), 7.66 (dd, 1 H, J = 5 Hz, J = 1 Hz), 7.32–7.08 (m, 7 H), 5.11 (m,1 H), 1.45 (d, 3 H, J = 5 Hz) |
| 2.5 | 15.9 | —CH(CH$_3$)$_2$ | 0.982 | 31.0 | | 8.43 (m, 1 H), 8.30 (bs, 1 H,), 8.09 (m, 1 H), 7.60 (d, 2 H, J = 5 Hz), 7.50–7.00 (m, 4 H) |
| 2.5 | 15.9 | CH$_3$ | 0.299 | 11.0 | | 8.37 (m, 1 H), 8.01 (dd, 1 H, J = 4 Hz, J = 1 Hz), 7.26 (m, 1 H), 6.70–6.42 (bs, 1 H), 2.98 (d, 3 H, J = 4 Hz) |

EXAMPLE 5

The following compounds of formula (I) are prepared according to the procedure of Example 3 from benzylamine and the appropriate 2-aryloxynicotinic acid reactants:

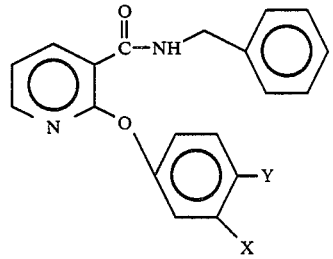

| Benzylamine | | 2-Aryloxy nicotinic acid | | | | Yield of (I) | | |
|---|---|---|---|---|---|---|---|---|
| G | mmol | X | Y | G | mmol | G | % | MP (°C.) |
| 1.04 | 9.74 | CN | H | 2.34 | 9.74 | 1.90 | 59.2 | 117–118 |
| 0.45 | 4.49 | OCH$_3$ | H | 1.00 | 4.08 | 1.03 | 75.7 | 102–103.5 |
| 0.62 | 5.83 | CF$_3$ | H | 1.50 | 5.30 | 1.20 | 60.8 | 90–91 |
| 0.72 | 6.74 | Cl | Cl | 1.74 | 6.12 | 1.34 | 58.8 | 108–110 |

| $^1$H NMR | | HRMS | |
|---|---|---|---|
| CDCl$_3$ δ | Formula | Calcd. | Found |
| 8.65 (dd, 1 H, J = 20 Hz, J = 5 Hz), 8.20 (dd, J = 10 Hz, J = 5 Hz), 7.95 (bs, 1 H), 7.56–7.18 (m, 10 H), 4.72 (d, 2 H, J = 10 Hz)* | C$_{20}$H$_{15}$N$_3$O$_2$ | 329.1158 | 329.1164 |
| 8.86 (dd, 1 H, J = 8 Hz, J = 2 Hz, 8.23 (dd, 2 H, J = 5 Hz, J = 2 Hz), 7.36–7.15 (m, 7 H), 6.84–6.68 (m, 3 H), 4.72 (d, 2 H), 3.76 (s, 3 H)* | | | |
| 8.62 (d, 1 H, J = 2.5 Hz), 8.19 (d, 1 H, J = 2 Hz), 8.02 (m, 1 H), 7.52 (s, 1 H), 7.39–7.18 (m, 9 H), 4.73 (d, 1 H, J = 5 Hz)** | C$_{20}$H$_{15}$N$_2$O$_2$F$_3$ | 372.1091 | 372.1086 |
| 8.62 (dd, 1 H, J = 7 Hz, J = 2 Hz), 8.18 (dd, 1 H, J = 2 Hz, J = 2 Hz), 7.95 (bs, 1 H), 7.45 (d, 1 H), 7.31–7.16 (m, 7 H), 6.97 | | | |

(dd, 1 H, J = 6 Hz), 4.68 (d, 2 H)**
*250 MHz
**300 MHz

EXAMPLE 6

N-(4-Fluorobenzyl)-2-(4-Fluorophenoxy)-nicotinamide

Sodium hydride dispersion, 60% by weight (167 mg, 4.2 mmol) and 25 ml dimethylformamide (DMF) is placed in a 65 ml round bottom flask equipped with a stir bar and a reflux condenser under nitrogen. P-fluorophenol (430 mg, 3.8 mmol) is added to the reaction mixture and stirred for one hour. The chloronicotinamide (850 mg, 3.2 mmol) is then added and the reaction heated to reflux for 16 hours. The mixture is then cooled to room temperature and poured into 50 ml of water. This is extracted with ethyl acetate (2×50 ml), and the combined organics washed with 1M NaOH (2×50 ml), water (2×50 ml) and brine (1×50 ml). The ethyl acetate is dried over anhydrous sodium sulfate, filtered and concentrated in vacuo to yield a green oil. This is digested in diethyl ether, and the resulting green crystals filtered off. The solids are recrystallized in ethanol to yield 283 mg (25.95%) of the title product as a white solid.

m.p.: 136.5°–138° C.

$^1$H NMR (300 MHz, CDCl$_3$) δ8.57 (dd, 1H, J=6 Hz, J=1Hz), 8.13 (m, 2H), 7.36-6.90 (m, 9H), 4.62 (d, 2H, J=5 Hz).

Analysis Calcd. for C$_{19}$H$_{14}$N$_2$O$_2$F$_2$: C, 67.05; H, 4.15; N, 8.23 Found: C, 66.04; H, 4.06; N, 8.23

HRMS 340.0994; Calcd. for C$_{19}$H$_{14}$N$_2$O$_2$F$_2$ 340.1020.

EXAMPLE 7

N-Benzyl-2-Phenoxy nicotinamide

Sodium hydride dispersion, 50% by weight (0.39 grams, 8.11 mmol) is placed into a 250 ml round bottom flask which is equipped with a stir bar and a reflux condenser under nitrogen and is charged with 80 ml DMF. Phenol (0.84 grams, 8.92 mmol) is added to the reaction mixture and allowed to stir for 20 minutes. The chloronicotinamide (2.00 grams, 8.11 mmol) is then added and the reaction heated to reflux for one hour. The reaction is then cooled to room temperature and 200 ml of water is added. The aqueous layer is extracted with ethyl acetate (2×50 ml), the extracts combined and are washed with 2N sodium hydroxide (2×200 ml) and water (1×200 ml). The organic layer is dried over anhydrous magnesium sulfate, filtered and concentrated in vacuo to yield an oil. The crude product is purified by flash chromatography using diethyl ether/hexane (2/1) as the eluant to yield 0.87 grams (35.2%) of the title aryloxynicotinamide as a white solid.

m.p.: 86°–87° C.

$^1$H NMR (90 MHz, CDCl$_3$) δ8.51 (dd, 1H, J=15 Hz, J=1 Hz), 8.05 (dd, 1H, J=10 Hz, J=3 Hz), 7.43-6.86 (m, 12H), 4.54 (d, 1H).

HRMS 304.1211 Calcd. for C$_{19}$H$_{16}$N$_2$O$_2$:304.1219.

EXAMPLE 8

N-Benzyl 2-(Exobicyclo[2.2.1]hept2-yloxy)-Nicotinamide Hydrochloride

Sodium hydride dispersion, 50% by weight (0.12 grams, 2.43 mmol) is placed into a 65 ml round bottom flask which is equipped with a stir bar and a reflux condenser under nitrogen and is charged with 20 ml dimethylformamide. Exo-norborneol (0.25 grams, 2.23 mmol) is added to the reaction mixture which is stirred for 20 minutes. The chloronicotinamide (0.50 grams, 2.03 mmol) is then added and the reaction heated to reflux for 3.5 hours. The reaction is then cooled to room temperature and 50 ml of water is added. The aqueous layer is extracted with ethyl acetate (2×50 ml). The organics are combined and are washed with water (4×50 ml). The organic layer is dried over anhydrous magnesium sulfate, filtered and concentrated in vacuo to yield an oil. The crude product is purified by flash chromatography using diethyl ether/hexanes (1/1) as the eluant to yield a clear oil. An HCl salt was formed with HCl saturated diethyl ether to yield 0.33 grams (45.3%) of the title product as a white solid.

m.p.: 200° C.

$^1$H NMR (250 MHz, CDCl$_3$) δ11.36 (vbs, 1H), 8.91 (dd, 1H, J=4 Hz, J=1Hz), 8.69 (dd, 1H, J=3.5 Hz, J=1 Hz), 7.84 (bs, 1H), 7.46-7.20 (m, 6H), 5.54 (d, 1H), 4.63 (dd, 2H, J=2.5 Hz, J=1 Hz), 2.40 (d, 1H), 2.25 (bs, 1H), 2.11 (m, 1H), 1.70-1.05 (m, 7H).

Analysis Calcd. for C$_{20}$H$_{22}$N$_2$O$_2$.HCl: C, 66.94; H, 6.46; N, 7.81 Found: C, 67.21; H, 6.28; N, 7.77.

EXAMPLE 9

N-Benzyl 2-(4-Fluorophenoxy)nicotinamide

Sodium hydride dispersion, 50% by weight (0.64 grams, 1.338 mmol) is placed into a 250 ml round bottom flask which is equipped with a stir bar and a reflux condensor under nitrogen and is charged with 120 ml dimethylformamide. 4-Fluorophenol (1.50 grams, 13.38 mmol) is added to the reaction mixture which is stirred for 30 minutes. The chloronicotinamide (3.00 grams, 12.16 mmol) is then added and the reaction heated to reflux for 1.5 hours. The reaction is then cooled to room temperature and 200 ml of water is added. The aqueous layer is extracted with ethyl acetate (2×175 ml). The organics are combined and washed with water (3×200 ml). The organic layer is dried over anhydrous magnesium sulfate, filtered and concentrated in vacuo to yield an oil. The crude product is purified by flash chromatography using diethyl ether as the eluant to yield 1.17 grams (29.8%) of the desired aryloxynicotinamide as a white solid.

m.p.: 102°–103° C.

$^1$H NMR (250 MHz, CDCl$_3$) δ8.66 (dd, 1H, J=9 Hz, J=2 Hz), 8.19 (dd, 1H, J=6 Hz, J=2 Hz), 8.18 (bs, 1H), 7.49-6.97 (m, 10H), 4.72 (d=2H).

Analysis Calcd. for C$_{19}$H$_{15}$N$_2$O$_2$F: C, 70.80; H, 4.69; N, 8.69 Found: C, 70.63; H, 4.59; N, 8.63.

In like manner, the following compounds (B) are prepared from the appropriate 2-chloronicotinamide (2-CNA) and 4-fluorophenol:

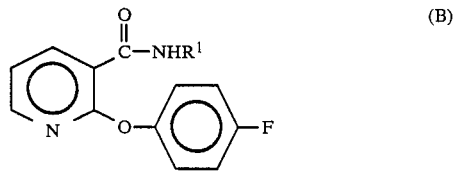
(B)

| R¹ | 2-CNA G | 2-CNA mmol | G | Yield of (B) % | MP(°C.) | ¹H NMR (300 MHz) CDCl₃ δ | Formula | HRMS Calcd | HRMS Found | Analysis Calcd C | Calcd H | Calcd N | Found C | Found H | Found N |
|---|---|---|---|---|---|---|---|---|---|---|---|---|---|---|---|
| 4-Cl benzyl | 1.0 | 3.6 | 0.260 | 20.2 | 124–126 | 8.62(dd, 1 H, J = 4 Hz, J = 1 Hz), 8.18 (m, 2 H), 7.27–7.08 (m, 9 H), 4.65 (d, 2 H, J = 4 Hz) | $C_{19}H_{14}N_2O_2ClF$ | 356.0728 | 356.0851 | 63.96 | 63.95 | 7.85 | 63.64 | 3.89 | 7.78 |
| 1-piperidyl | 1.5 | 6.7 | 0.155 | 7.7 | 138.5–141 | 8.11(m, 1 H), 7.69, (dd, 1 H, J = 4 Hz, J = 1 Hz) 7.10–7.00 (m, 5 H), 3.84–3.62 (bs, 2 H), 3.46–3.22 (d, 2 H, J = 18 Hz), 1.82–1.44 (t, 6 H) | $C_{17}H_{17}N_2O_2F$ | 300.1219 | 300.1219 | 67.98 | 5.71 | 9.33 | 66.71 | 5.46 | 9.15 |
| 1-(1-phenethyl) | 2.5 | 9.6 | 1.4 | 43.3 | 118–119.5 | 8.56(dd, HH, J = 4 Hz, J = 1 Hz), 8.20–8.06 (m, 2 H), 7.40–7.18 (m, 5 H), 5.33 (m, 1 H), 1.56 (d, 3 H, J = 5 Hz) | $C_{20}H_{17}N_2O_2F$ | 336.1274 | 336.1249 | 71.41 | 5.10 | 8.33 | 70.72 | 4.94 | 8.25 |
| phenyl | 1.7 | 7.3 | 0.95 | 42.4 | 133–135 | 9.70(s, 1 H), 8.66 (dd, 1 H, J = 4 Hz, J = 1 Hz), 8.21 (m, 1 H), 7.64 (d, 2 H, J = 5 Hz), 7.35 (t, 2 H), 7.30–6.96 (m, 6 H) | $C_{18}H_{13}N_2O_2F$ | 308.096 | 308.959 | 70.12 | 4.25 | 9.09 | 70.35 | 4.31 | 9.12 |
| isopropyl | 0.940 | 4.7 | 0.484 | 33.4 | 104–106 | 8.57(dd, 1 H, J = 4 Hz, J = 1 Hz), 8.15 (m, 1 H) | $C_{15}H_{15}N_2O_2F$ | 274.112 | 274.1104 | 65.68 | 5.51 | 10.22 | 65.85 | 5.58 | 10.24 |
| methyl | 0.290 | 1.7 | 0.148 | 35 | 167–170 | 8.56(dd, 1 H, J = 4 Hz, J = 1 Hz), 8.11 (m, 1 H), 7.84–7.60 (bs, 1 H), 7.18–6.90 (m, 5 H), 3.01 (d, 3 H, J = 4 Hz) | $C_{13}H_{11}N_2O_2F$ | 246.080 | 246.0778 | 63.40 | 4.50 | 11.38 | 63.34 | 4.51 | 11.33 |
| 4-CH₃ benzyl | 0.834 | 3.2 | 0.501 | 46.5 | 64.5–66 | 8.60(dd, 1 H, J = 4 Hz, J = 1 Hz), 8.22–8.04 (m, 2 H), 7.30–7.04 (m, 9 H), 4.65 (d, 2 H, J = 4 Hz), 2.32 (s, 3 H) | $C_{20}H_{17}N_2O_2F$ | 336.1274 | 336.1307 | 71.41 | 5.10 | 8.33 | 71.11 | 5.10 | 8.23 |
| 4-CH₃O benzyl | 1.0 | 3.6 | 0.507 | 39.9 | 76.5–78 | 8.61(dd, 1 H, J = 4 Hz, J = 1 Hz), 8.22–8.00 (m, 2 H), 7.38–6.92 (m, 7 H), 6.82 (d, 2 H, J = 6 Hz), 4.62 (d, 2 H, J = 4 Hz), 3.77 (s, 3 H) | $C_{20}H_{17}N_2O_3F$ | 352.1223 | 352.1246 | 68.17 | 4.86 | 7.95 | 68.13 | 4.95 | 7.91 |

EXAMPLE 10

Following the procedure of Example 9, the 2-aryloxynicotinic acids having the formula

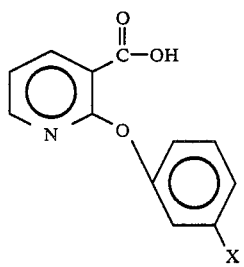

are prepared from equimolar amounts of 2-chloronicotinic acid (2-CNA) and the appropriate phenol.

| 2-CNA | | Product Yield | | | | ¹H NMR | | HRMS | |
|---|---|---|---|---|---|---|---|---|---|
| G | mmol | X | G | % | MP (°C.) | MHz | Solvent δ | Calcd | Found |
| 5.00 | 31.73 | 3-CN | 2.34 | 30.7 | | 90 | DMSO-d₆ 8.25 (d, 2 H, J = 18 Hz), 7.63–7.10 (m, 6 H) | | |
| 5.00 | 31.73 | 3-OCH₃ | 3.95 | 50.8 | 166.5–168 | 250 | DMSO-d₆ 8.38–8.20 (m, 2 H), 7.33–7.21 (m, 2 H), 6.80–6.62 (m, 3 H), 3.75 (s, 3 H) | | |
| 5.00 | 31.73 | 3-CF₃ | 4.74 | 52.7 | 140–144 | 300 | DMSO-d₆ 8.29–8.26 (m, 2 H), 7.67 (m, 2 H), 7.45 (m, 2 H), 7.27 (dt, (1 H, J = 4 Hz) | 283.0452 | 283.0457 |

EXAMPLE 11

2-(3,4-Dichlorophenoxy)nicotinic Acid

Sodium hydride dispersion, 60% by weight (2.54 grams, 63.47 mmol) is placed into a 125 ml round bottom flask equipped with a stir bar and condenser under nitrogen and is charged with 32 ml of dimethyl formamide. 3,4-Dichlorophenol (5.17 grams, 31.73 mmol) is added portionwise over five minutes. During this addition, an exotherm and vigorous gas evolution are observed. The reaction is allowed to stir for five minutes. 2-Chloronicotinic acid (5.00 grams, 31.73 mmol) is then added portionwise over five minutes. When gas evolution subsides, the reaction is heated to reflux for 21 hours. It is then cooled to room temperature and 300 ml of water added. The aqueous layer is extracted with diethyl ether ($3 \times 200$ ml), then pH adjusted to acidic with glacial acetic acid and stirred. After 2 hours, the precipitate which has formed is filtered and washed with ($3 \times 100$ ml) water then ($3 \times 100$ ml) pentane to yield 1.78 grams (19.8%) of product as a tan crystalline solid.

¹H NMR (90 MHz, DMSO-d₆): δ8.30–8.25 (m, 2H), 8.00–7.05 (m, 5H).

EXAMPLE 12

N-Benzyl-[2-(3-Carboxyphenoxy)]nicotinamide

Sodium hydride dispersion, 60% by weight (1.71 grams, 42.56 mmol) is placed into a 250 ml round bottom flask equipped with a stir bar and condenser under nitrogen and is charged with 100 ml of dimethylformamide. m-Hydroxybenzoic acid (2.80 grams, 20.27 mmol) is added to the reaction mixture which is stirred 20 minutes. N-benzyl-2-chloronicotinamide (5.00 grams, 20.27 mmol) is then added and the reaction heated to reflux for 18 hours. It is then cooled to room temperature, 300 ml of water added, and the aqueous layer extracted with diethyl ether ($2 \times 100$ ml). The aqueous layer is then pH adjusted to acidic with acetic acid and the precipitate which forms is filtered off. This crude material is purified by flash chromatography using ethyl acetate as the eluant to yield 3.44 grams (48.7%) of the title product as a white solid.

m.p.: 157°–158° C.

¹H NMR (300 MHz, CDCl₃) δ8.66 (dd, 1H, J = 8 Hz, J = 2H), 8.19 (dd, 1H, J = 5 Hz, J = 2 Hz), 8.11 (m, 1H), 7.98 (dt, 1H, J = 6 Hz, J = 2 Hz), 7.84 (t, 1H, J = 2 Hz), 7.52 (t, 1H, J = 8 Hz), 7.38–7.16 (m, 7H), 4.71 (d, 2H, J = 6 Hz).

HRMS: 348.1110 Calcd. for C₂₀H₁₆N₂O₄, 348.1085.

EXAMPLE 13

N-Benzyl-2-(3-Carboisobutoxyphenoxy)nicotinamide

N-Benzyl-2-(3-carboxyphenoxy)nicotinamide (2.00 grams, 5.74 mmol) is placed into a 100 ml 3-neck round bottom flask equipped with magnetic stir bar, thermometer, nitrogen inlet and a rubber septum. The flask is charged with 30 ml of THF and N-methyl-morpholine (0.68 grams, 6.73 mmol) is added via syringe. The reaction is chilled to $-10°$ C. and isobutyl chloroformate (0.92 grams, 6.73 mmol) added to the reaction via syringe while maintaining the temperature at less than 0° C. The reaction is stirred at $-10°$ C. for 20 minutes. Methanol (1.75 ml) is then added via syringe while maintaining the temperature below 0° C. The reaction is allowed to slowly warm to room temperature. After stirring for 2 hours, 2N sodium hydroxide (50 ml) is added to the reaction. This is then extracted with ethyl acetate ($1 \times 100$ ml). The organics are washed with 2N sodium hydroxide ($3 \times 50$ ml). The organic layer is dried over anhydrous magnesium sulfate, filtered and concentrated in vacuo to yield an oil. The crude product is purified by flash chromatography with diethyl ether as the eluant to yield 0.63 grams (27.2%) of the title product as a white solid.

m.p.: 96°–97° C.

¹H NMR (300 MHz, CDCl₃) δ8.65 (dd, 1H, J = 6 Hz, J = 2 Hz), 8.18 (dd, 1H, J = 4 Hz, J = 1Hz), 8.16 (bs, 1H), 7.97 (d, 1H), 7.82 (t, 1H, J = 2 Hz), 7.52 (t, 1H, J = 8 Hz), 7.42–7.17 (m, 7H), 4.71 (d, 2H), 4.10 (d, 2H), 1.55 (m, 1H), 0.97 (d, 6H).

HRMS: 404.1736 Calcd. for C₂₄H₂₄N₂O₄, 404.1730.

EXAMPLE 14

N-Benzyl 2-(3-methylcarbamoylphenoxy)nicotinamide

N-Benzyl 2-(3-carboxyphenoxy)nicotinamide (1.00 gram, 2.87 mmol) is placed into a 100 ml 3-neck round bottom flask equipped with magnetic stir bar, thermometer, nitrogen inlet and a rubber septum. The flash is charged with 15 ml of THF and N-methylmorpholine (0.29 grams, 2.87 mmol) is added via syringe. The reaction is chilled to −10° C. and isobutyl chloroformate 0.39 grams, 2.87 mmol) added to the reaction via syringe while maintaining the temperature at less than 0° C. The reaction is stirred at −10° C. for 30 minutes. Monomethylamine gas is bubbled into the reaction via syringe while maintaining the temperature below 0° C. The reaction is allowed to slowly warm to room temperature. After stirring for 2½ hours, water (20 ml) is added to the reaction which is then extracted with ethyl acetate (2×100 ml). The organics are combined and washed with 2N sodium hydroxide (4×75 ml) and (1×100 ml) water. The organic layer is dried over anhydrous magnesium sulfate, filtered and concentrated in vacuo to yield a paste. The crude product is purified by trituration with diethyl ether to yield 0.63 grams (60.6%) of the title product as a white solid.

m.p.: 164°–167° C.

$^1$H NMR (300 MHz, CDCl$_3$) δ8.62 (dd, 1H, J=5 Hz, J=1 Hz), 8.17 (dd, 1H, J=3 Hz, J=1 Hz), 8.12 (bs, 1H), 7.60 (t, 2H, J=5 Hz), 7.47 (t, 1H, J=2.5) 7.40–7.14 (m, 6H), 6.12 (bs, 1H), 4.70 (d, 2H, J=5 Hz).

In like manner, N-benzyl 2-(3-dimethylcarbamoylphenoxy)nicotinamide is prepared but substituting dimethylamine for monomethylamine. Yield =0.35 grams (32.4%) of a tan oil.

$^1$H NMR (300 MHz, CDCl$_3$) δ8.65 (dd, 1H, J=6 Hz, J=1Hz), 8.17 (dd, 1H, J=2 Hz, J=1 Hz), 8.15 (bs, 1H), 7.44 (t, 1H, J=8 Hz), 7.35–7.14 (m, 10H), 4.69 (d, 2H, J=6 Hz), 3.04 (bd, 6H, J=22 Hz).

EXAMPLE 15

N-Benzyl 2-(3-carbomethoxyphenoxy)nicotinamide

N-Benzyl 2-(3-carboxyphenoxy)nicotinamide (1.00 gram, 2.87 mmol) is slurried in 12 ml of methanol in a 125 ml round bottom flask equipped with magnetic stir bar and nitrogen source and chilled to 0° C. Acetyl chloride (0.57 ml) is added to the flask and the reaction allowed to slowly warm to room temperature. After 18 hours the reaction is quenched by adding 50 ml of 2N sodium hydroxide solution. It is then extracted (2×50 ml) with ethyl acetate, the combined extracts washed with (2×100 ml) 2N sodium hydroxide and dried over anhydrous magnesium sulfate. Filtration and concentration of the extract in vacuo yield a pasty solid which is purified by trituration with diethyl ether to yield 0.38 grams (36.5%) of the title product as a white crystalline solid.

m.p.: 119°–120° C.

$^1$H NMR (300 MHz, CDCl$_3$) δ8.65 (m, 1H), 8.19–8.12 (m, 2H), 7.95 (dd, 1H, J=8 Hz, J=1 Hz), 7.79 (bs, 1H), 7.9 (t, 1H, J=7 Hz), 7.35–7.15 (m, 7H), 4.70 (d, 2H), 3.89 (s, 3H).

We claim:

1. A compound having the formula

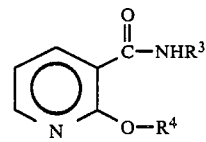

or a pharmaceutically acceptable acid addition salt thereof wherein

R$^3$ is 1-piperidyl, 1-(3-indolyl)ethyl, (C$_{1-4}$)-alkyl, phenyl, benzyl, 1-(1-phenylethyl) or monosubstituted benzyl wherein the substituent is chloro, fluoro, methyl or methoxy and said substituent is on the aromatic ring;

R$^4$ is bicyclo[2 2.1]hept-2-yl or

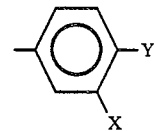

wherein Y is hydrogen, fluoro or chloro; and

X is hydrogen, fluoro, chloro, methoxy, trifluoromethyl, cyano, carboxy, methylcarbamoyl, dimethyl-carbamoyl or carbo(C$_{1-4}$ alkoxy);

provided that when R$^3$ is phenyl, benzyl, monosubstituted benzyl, 1-(1-phenylethyl) or (C$_{1-4}$)alkyl, R$^4$ is bicyclo[2.2.1]hept-2-yl.

2. A compound according to claim 1 wherein R$^3$ is 1-piperidyl or 1-(3-indolyl)ethyl.

3. The compound according to claim 2 wherein R$^3$ is 1-(3-indolyl)ethyl and R$^4$ is bicyclo[2.2.1]hept-2-yl.

4. A compound according to claim 2 wherein R$^4$ is

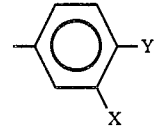

wherein Y is hydrogen and X is carbo(C$_{1-4}$ alkoxy).

5. The compound according to claim 4 wherein R$^3$ is 1-piperidyl and R$^4$ is

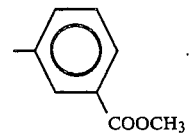

* * * * *